United States Patent [19]
Chen

[11] Patent Number: 5,955,323
[45] Date of Patent: *Sep. 21, 1999

[54] **AUTOMATED HIGH-YIELD FERMENTATION OF PLASMID DNA IN *ESCHERICHIA COLI***

[75] Inventor: Wei Chen, Frazer, Pa.

[73] Assignee: American Home Products Corporation, Madison, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/691,177

[22] Filed: Aug. 1, 1996

[51] Int. Cl.$^6$ ............................... C12P 19/34; C12N 1/20
[52] U.S. Cl. ..................... 435/91.1; 435/89; 435/252.8; 435/259
[58] Field of Search ..................... 435/91.1, 89, 252.8, 435/259

[56] References Cited

U.S. PATENT DOCUMENTS

| | | | |
|---|---|---|---|
| 4,891,310 | 1/1990 | Shimuzu et al. | 435/3 |
| 4,894,334 | 1/1990 | Ben-Basset et al. | 435/69.1 |
| 5,206,154 | 4/1993 | Lai et al. | 435/69.7 |
| 5,445,948 | 8/1995 | Shimizu et al. | 435/69.7 |

FOREIGN PATENT DOCUMENTS

| | | | |
|---|---|---|---|
| DD 290215 A5 | 5/1991 | Germany . | |
| WO96/40905 | 12/1996 | WIPO . | |

OTHER PUBLICATIONS

Cutayar et al., "High Cell Density Culture of *E. Coli* in a Fed–Batch System with Dissolved Oxygen as Substrate Feed Indicator", *Biotech Letter*, 1989, 11(3), 155–160.

Fieschko et al., "Production of Human Alpha Consensus Interferon in Recombinant *Escherichia coli*", *Chem. Eng. Comm.*, 1986, 45, 229–240.

Flodh, "Human Growth Hormone Produced with Recombinant DNA Technology: Development and Production", *Acta Paediatr. Scand.* [Suppl], 1986, 325, 1–9.

Kim et al., "Production of Poly–β–Hydroxybutyrate by Fed–Batch Culture of Recombinant *Escherichia Coli*", *Biotech Letter*, 1992, 14(9), 811–816.

Mori et al., "High Density Cultivation of Biomass in Fed–Batch System with Do–Stat", *J. Of Chem. Engin. of Japan*, 1979, 12(4), 313–319.

Nishio et al., "A Fed–Batch Culture of Methanol–utilizing Bacteria with pH Stat", *J. Ferment. Tech.*, 1977, 55(2), 151–155.

Wang et al., "Computer–Aided Baker's Yeast Fermentations", *Biotech. Bioeng.*, 1977, 19, 69–86.

Yamane et al., "Semi–batch Culture of Methanol–assimilating Bacteria with Exponentially Increased Methanol Feed", *J. Ferment. Tech.*, 1976, 54(4), 229–240.

Yano et al., "Fed–batch Culture of Methanol–utilizing Bacterium with DO-stat", *J. Ferment Tech.*, 1978, 56(4), 416–420.

Zabriskie et al., "Factors influencing productivity of fermentations employing recombinant microorganisms", *Enzyme Microb. Tech.*, 1986, 8, 706–717.

*Primary Examiner*—Leon B. Lankford, Jr.
*Attorney, Agent, or Firm*—Howson and Howson

[57] ABSTRACT

This invention relates to a fermentation process for high-yield production of plasmid DNA in *E coli* strains. In the disclosed process, a slow growth rate of cells is controlled and maintained by an automated nutrient feed scheme based on dissolved oxygen concentration (DOC) and pH. This controlled slow growth rate promotes high plasmid DNA stability during host cell replication. As a result, high yield production of plasmid DNA is achieved.

33 Claims, 3 Drawing Sheets

AUTOMATED HIGH-YIELD FERMENTATION OF PLASMID DNA IN ESCHERICHIA COLI

FIELD OF THE INVENTION

This invention relates to a fermentation process for high-yield production of plasmid DNA in *E.coli* strains. In the disclosed process, a slow growth rate of *E.coli* cells is controlled and maintained by an automated nutrient feed scheme based on dissolved oxygen concentration (DOC) and pH. This controlled slow growth rate allows high plasmid DNA stability during the host cell replication. As a result, high yield production of plasmid DNA is achieved. The method of this invention has the following advantages when used as a manufacturing process for plasmid DNA production:

1. Easy to operate and highly reproducible due to its automated nutrient feeding control scheme.
2. Applicable to a variety of DNA plasmids and *E. coli* host strains, because the nutrient concentration-associated changes in DOC and pH are common phenomena in certain media formulations.
3. Various desired growth rates may be achieved by adjusting the nutrient feed rate with different set points of DOC and pH.

BACKGROUND OF THE INVENTION

Fermentation has long been a key technology for mass production of biological products. An economically sound fermentation process usually has to demonstrate the following advantages: optimal cell production, maximum product accumulation and minimum nutrient consumption. In most industrial applications, fed-batch cultures have been found preferable over batch cultures because during a fed-batch fermentation an optical cell growth rate and nutrient consumption rate can be achieved by controlling the nutrient feeding in a desired range. A successful fed-batch culture can reach a maximum cell density of over 100 g/L cell dry weight (Mori et al., *Journal of Chemical Enqineerinq of Japan* 12:313–39(1979)). Thus the highest levels of volumetric productivity can be achieved. In a batch culture it is generally necessary to provide a high initial concentration of nutrients in order to sustain cell growth over an extended time. As a result, substrate inhibition may occur in the early stages of cell growth, followed by a nutrient deficiency in the late stages of fermentation. Consequently, an optimal cell growth rate and product accumulation rate can hardly be obtained in a batch culture.

A number of nutrient feeding strategies have been explored as a means of controlling cell growth in fed-batch cultures. The strategies can be divided into two groups: non-feed-back control and feed-back control. The former includes controlling the nutrient feeding rate according to a pre-determined, constant or exponential profile (Yamane et al., *J.Ferment.Technol*. 54:229–240(1976)). This type of feeding scheme requires that the cell performs reproducibly each time in both the inoculum and early batch culture stages to warrant the match of the feeding rate to the actual cell growth rate. This is a kind of very stringent control which may work very consistently, but could easily get off track if cell activity changes due to any environmental fluctuation. Feed-back control, on the other hand, can react based on demand and is directly correlated to the cell activities actually existing throughout the fermentation. The control parameters which have been used for feed-back controls include respiratory quotient (Wang et al., *Biotechnol.Bioeng.* 19:69–81(1977)); pH (Nishio et al., *J.Ferment. Technol*.55:151–155(1977)), (Kim et al., *Biotechnol Lett.* 14:811–816(1992)); or DOC (Mori et al., *Journal of Chemical Encineering of Japan* 12:313–39(1979)), (Yano et al., *J. Ferment. Technol*. 56:416–420(1978)), (Cutayar et al., *Biotechnol Lett*. 11:155–160(1989)).

With the advancement of recombinant DNA technology, the above fermentation technology has been further developed for production of recombinant proteins in recombinant organisms such as *E.coli* and many other cell cultures. A number of recombinant proteins which are produced by fermentation technology such as recombinant human insulin (Humulin®, Lilly), recombinant erythropoietin (Epogen®, Amgen), recombinant tissue plasminogen activator (Activase®, Genentech), and recombinant interferon (Roferon®, Roche), are now available for human pharmaceutical use.

Some of these successful production fermentation processes for recombinant proteins have also been published in scientific journals or patents (Fieschko et al., *Chem. Eng. Commun.* 45:229–240(1986)), (Riesenberg et al., Patent No. DD290215(1991)). However, most production scale fermentation processes (published or unpublished) for recombinant proteins are either a batch culture (*Flodh. Acta Paediatr. Scand.* 325:1–9.(1986)) or a fed-batch batch culture with a manual feed control scheme ((Fieschko et al., *Chem. Eng. Commun.* 45:229–240(1986)). These processes are hardly reproducible, and require labor-intensive "baby sitting" by experienced personnel. Moreover, the conditions under which the process is operated are certainly not optimized.

Most biotechnology companies do not spend time in developing an efficient fermentation process with an optimized control strategy because they frequently face short deadlines in putting their products on the market. Another reason is related to regulatory compliance. Some believe that an automated fermentation process with optimized computer controls is too complicated for validation purposes. As a result, few feed-back controlled fermentation processes have ever been developed for pharmaceutical production purposes.

More recently, it has been shown that plasmid DNA can be used as a non-viral gene delivery system for clinical applications (Wang et al., *Proc. Nat'l. Acad. Sci. USA* 90:4156–4160 (1993). For such applications, which include gene therapy and genetic immunization, the plasmids themselves rather than the expressed proteins are the desired pharmaceutical products. Accordingly, there is a need for pharmaceutically acceptable large scale processes for production of intact plasmid DNA. Although it is natural to think that it might be possible to produce plasmid DNA with the fermentation technology developed for recombinant proteins, the biological processes involved are fundamentally different due to different end products: plasmid DNA vs. protein. Since cells are required to produce plasmid DNA in large quantities rather than proteins, precursor pools will be different: nucleotides vs. amino acids. Secondly, plasmid production requires a different synthetic pathway than protein: DNA replication vs. transcription and translation. Thirdly, plasmid DNA is susceptible to degradation by nucleases rather than proteases. The undesired by-products of plasmid production will also be different: proteins, RNA, chromosomal DNA and other forms of DNA vs. DNA and RNA for protein products. Furthermore, in order to obtain a high yield of plasmid DNA at the end of fermentation, cell growth rate may need to be regulated because a fast (close to maximum) growth rate may result in significant plasmid loss during fermentation (Zabriskie et al. *Enzyme Microb. Technol.* 8:706–717(1986)). These factors may require special control strategies for fermentation of plasmid DNA. Specifically, an optimal cell growth rate and nutrient environment have to be identified and maintained to sustain a high plasmid DNA stability and-integrity.

Recombinant bacterial plasmids for pharmaceutical applications typically contain large segments of insert DNA for disease targets, as well as the expression vectors themselves which typically comprise marker genes for selection purposes, origin sequences for DNA replication in bacteria, and eukaryotic promoter and other regulatory sequences for expression in mammalian cells. Such plasmid molecules tend to be large, on the order of $10^6$–$10^7$ daltons(5–20 kb), and particularly susceptible to mutations during fermentation. Therefore, a successful plasmid fermentation process has to provide a culture environment which maximizes the conversion of energy and substrates to plasmid DNA with high stability and integrity, while minimizing other by-products such as protein, RNAs and other DNAs as much as possible.

This invention demonstrates that the above goals can be achieved through a careful medium formulation and an automated feed-back controlled nutrient feeding strategy based on DOC (dissolved oxygen concentration) and pH. The process is based on the principle that when the carbon source in the culture is about to be completely depleted, DOC will rise rapidly. This is presumably due to a slowing down of respiratory activity (i.e., oxidative reactions). If the demand for the carbon source is not met, the pH of the culture will rise too. This phenomenon is probably caused by the consumption of metabolic fatty acids (e.g., acetic acid et al.) by cells as an alternative carbon source. The increase in pH could also be caused by production of ammonium ions as a result of protein degradation. Based upon the above, we designed an automated process using both pH and DO controllers to control the nutrient feeding rates. The DO controller also controls the agitation rate and the pH controller also controls the addition of base to the fermentation medium. By adjusting DO and pH control set points, the cell specific growth rate was decreased about 10 fold. As a result, plasmid DNA yield was increased by about 10 fold.

DETAILED DESCRIPTION OF THE INVENTION

Figure 1:
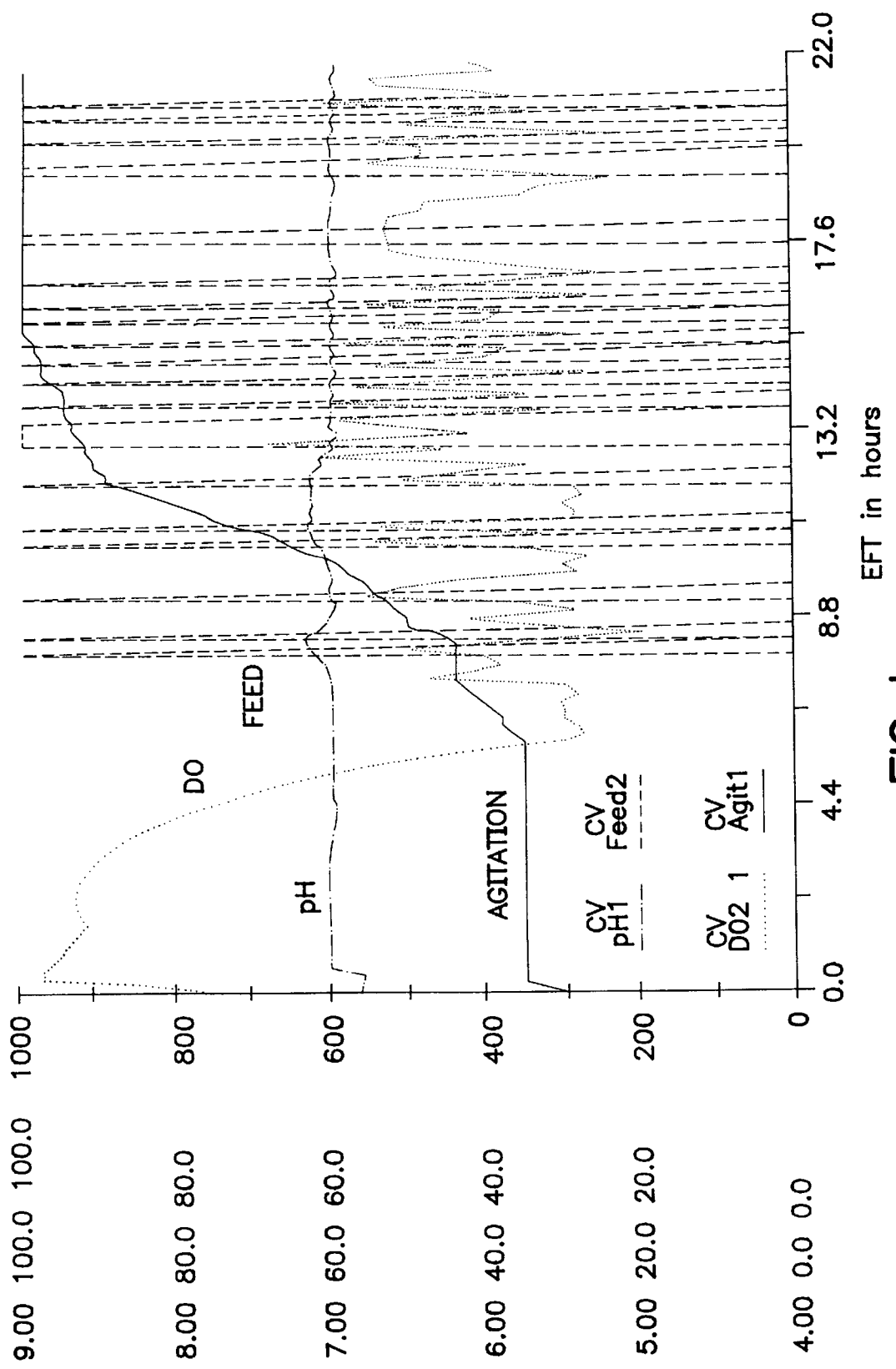
FIG. 1. Time course of the controlling parameters: pH and DO. Agitation and nutrient pump output during the DO/pH stat feed-back controlled fermentation.

Seed culture preparation.

*E.coli* strain DH10b (Gibco BRL, Life Technologies, Inc., Gaithersburg, Md.) containing a 7.2 Kb plasmid with Col E1 origin and HIV-1 env gene was cultured in a flask of seed medium on a rotary shaker at 37° C. for 16 hours. The seed medium consisted of $Na_2HPO_4$ 6 g, $KH_2PO_4$ 3 g, $(NH_4)_2SO_4$ 3 g, $MgSO_4.7H_2O$ 0.25 g, glucose 5 g, and yeast extract log per liter. The seed volume is 1% of fermentor batch medium. The growth of the seed was measured by optical density at 600 nm with Spectrophotometer UV-1201 (Simadzu, Columbia, Md.). A typical OD range of 3–4 was seen after 16 hours of incubation.

Fermentor Operation.

A lab scale fermentation was carried out in a 7L stirred reactor, Bioflo3000 (New Brunswick Scientific, Edison, N.J.). The reactor was equipped with a built-in digital controller for pH, temperature, agitation, DO and a nutrient feed pump. The above control parameters could also be set and controlled using the AFS fermentation process software through a PC (Advanced Fermentation Software, Ver. 3.42, New Brunswick Scientific Co., Edison, N.J.). The AFS software is designed to monitor such common parameters as temperature, pH, DOC, and agitation.

In this experiment, the control scheme is as follows: The pH controller drives a base pump and the DO controller can control agitation speed through assigning controlling set points on the AFS software. If the value of the pH drops below the set point (7.0), the controller will automatically activate a peristaltic pump to add $NH_4OH$ until the pH is brought back to 7.0. If the DOC drops below the set point (30%), the controller will send signals to increase the agitation speed until the DOC rises above the set point. When the DOC set point is reached agitation rate will remain unchanged until a further increase is triggered. The above set points can be set either on the controllers or on the AFS software. The nutrient is fed via a peristaltic pump which is controlled through the programming of the AFS software as below: if DOC >50%, or pH >7.2, the nutrient pump=1 (i.e., activated); if DOC <50% and pH <7.2, the pump=0 (i.e., inactivated). The controllers constantly monitor the fermentation medium and send the signals to the PC via the AFS software. If the pH >7.2 or DOC >50%, the software will send signals to activate the nutrient pump. If the pH <7.2 and DOC <50%, the nutrient pump will be inactivated.

Accordingly, the process of the invention contemplates two controllers constantly monitoring the fermentation medium: the pH controller and the DOC controller. In one embodiment of the invention each controller has a high and a low setpoint, each of which automatically triggers a different response, e.g., addition of nutrient of addition of base. In another embodiment of the invention, the controllers do not directly effect the desired response, but the signals from the controllers are fed into a computer, which is programmed with "effective" set points that direct the desired responses. It is also possible for one controller to directly trigger the desired responses and the other controller to work through a computer. Therefore, one of skill in the art will recognize that any reference herein to setpoints contemplates both actual and effective setpoints. In all cases, however, there will always be a lower setpoint and a higher setpoint, each of which triggers a different response, and there must always be a gap between these setpoints.

Accordingly, the pH controller will have a lower setpoint, generally between about 6.8 and 7.0, preferably about 7.0, which triggers the addition of base. The pH controller will also nave a higher setpoint, generally between about 7.05 and 7.2, preferably between about 7.1 to 7.2, more preferably about 7.2, which triggers the addition of nutrient medium. The DOC controller will have a lower setpoint, typically between about 10% and 50%, preferably between about 20% and 40%, more preferably about 30%, that triggers increased agitation. The DOC controller will also have a higher setpoint, generally between about 40% to 70%, preferably between about 45% to 55%, more preferably about 50%, that triggers nutrient feed. Therefore, the addition of nutrient is automatically triggered, independently, by pH rising above the setpoint or DOC rising above the setpoint, whereas DOC dropping below the set point automatically triggers increased agitation, and pH dropping below the set point automatically triggers the addition of base. These several automatic feed-back controls, which are linked to cell-growth phenomena, serve to keep cell growth controlled at a desirable rate for plasmid production.

An initial 4 L of fermentor batch medium with the same composition as the seed medium was inoculated with 1% (v/v) of the seed. During the fermentation, pH was controlled at 7.0 with 33% of $NH_4OH$. Temperature was controlled at 37° C. In the first 5 hours of fermentation, *E. coli* cells utilized the batched-in nutrients and grew in a batch mode. As shown in FIG. 1, DOC decreased gradually as cell growth progressed. To prevent DOC from dropping below 30% of saturation, the agitation speed was controlled by DOC at a set point of 30% and programmed via AFS so that every time DOC fell below 30%, the agitation speed automatically increased by 1% in every 30 seconds, until DOC rose back above 30%. After DOC rises above 30% the agitation rate remains at the higher speed. If DOC again drops below 30% agitation will again automatically increase by 1% in every 30 seconds.

Meanwhile, at 5 hours of fermentation, when nutrients were almost consumed, DOC was leveling off and then began to rise rapidly. So was pH. At this point, a concentrated nutrient solution (40% glucose/20% yeast extract) was fed into the culture via a nutrient pump. Activation of the nutrient pump was triggered independently by either DOC or pH at respective set points of 50% and 7.2 via the controllers and AFS. The control of the nutrient feed was programmed so that when either DOC or pH rose above the set points (50% and 7.2, respectively) due to nutrient depletion, the pump started to feed the nutrients. Thus, the cells resumed growth, bringing DOC and pH down to below the set points. Once either DOC or pH dropped below the set points due to nutrient accumulation, the nutrient pump was automatically inactivated, which completed one cycle. If DOC dropped below the set point, agitatio speed would increase as described above. Cell growth accelerated, and as nutrient again became depleted, DOC and pH began to rise. Thus, another cycle started.

As shown in FIG. 1., controlling both agitation and nutrient feeding worked in a well-coordinated way to ensure a sufficient nutrient and oxygen supply for cells to-grow at a desired growth rate without either over- or underfeeding the nutrients. A desired cell growth rate could be achieved by adjusting the control window. In this case, we used 50% of DOC for nutrient feed and 30% of DOC to control agitation. DOC setpoints of 30% to trigger agitation and 50% to trigger nutrient feed produced especially good results. If we raised the upper setpoint to 60% DOC to trigger nutrient feed and lowered the lower DOC setpoint to 20% for agitation, a slower cell growth rate could be expected. Changing the window between 30% and 40% DOC, a faster growth rate should be attained. DOC setpoints ranging between 10% to trigger agitation and 70% to trigger nutrient feed are expected to result in even slower cell growth characteristics.

Figure 2:
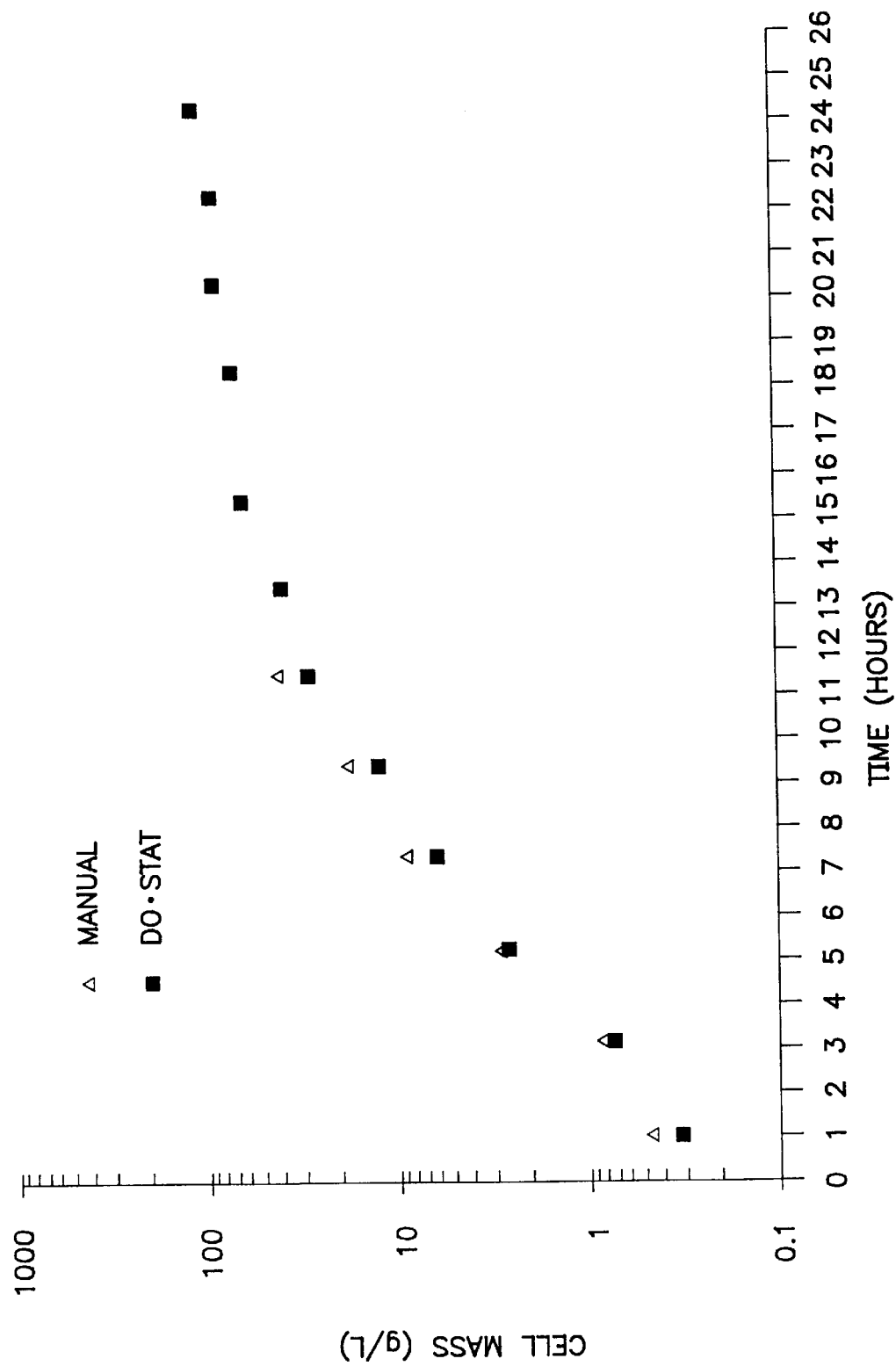
FIG. 2. Profiles of cell growth in the DO/pH stat feed-back controlled fermentation and a manual fed-batch culture.

Using the above control strategy, we were able to slow down the cell growth rate by about 10 fold, compared to a fed-batch culture using a manual nutrient feed (FIG. 2). In the manual fed-batch culture with the same medium composition, a maximum specific growth rate (averaged about 0.4 $h^{-1}$ in FIG. 2) was maintained and the cells were entering stationary phase at 11 hours. This is because the manual feeding method could hardly catch up with cell demand for nutrients. It was necessary therefore to maintain a high nutrient concentration in the culture to avoid nutrient starvation. Typically, an OD of 30 was obtained. When the cells were grown at such a fast rate, most of the substrates and energy would be used wastefully for building cell mass and end products such as acetate and $CO_2$. Furthermore, plasmid loss due to failed replication and/or partition would result. Contrary to the manual fed-batch culture, the process of this invention controlled specific cell growth rate down to 0.04 $h^{-1}$ because of the feed-back controlled nutrient feed, which was optimized according to demand. As a result, cells sustained extended growth with a final OD of over 100 after 22 hours of fermentation (FIG. 2).

Throughout the course of the fermentation, broth samples were taken periodically. Plasmid DNA was purified according to the method of Maniatis (*Molecular Cloning: A Laboratory Manual*, Volume 1, page 1.38, Cold Spring Harbor Laboratory Press (1989)). After purification, the supercoiled plasmid DNA was quantitated as follows: supercoiled DNA was separated on a 0.8% agarose gel and banding patterns photographed with a Polaroid camera. The image was captured by a ScanMan™ 256 (Logitech, Fremont, Calif.) with the FotoTouch™ Color software. The quantitation was done through calculation by software ImageQuant™ (Molecular Dynamics, Inc. San Jose, Calif.) based on purified standard DNA. Quantitation was also verified by HPLC method through injecting 30 μL samples into a Nucleogen DEAE 4000-7 Anion exchange column (Waters, Mass.).

Figure 3:
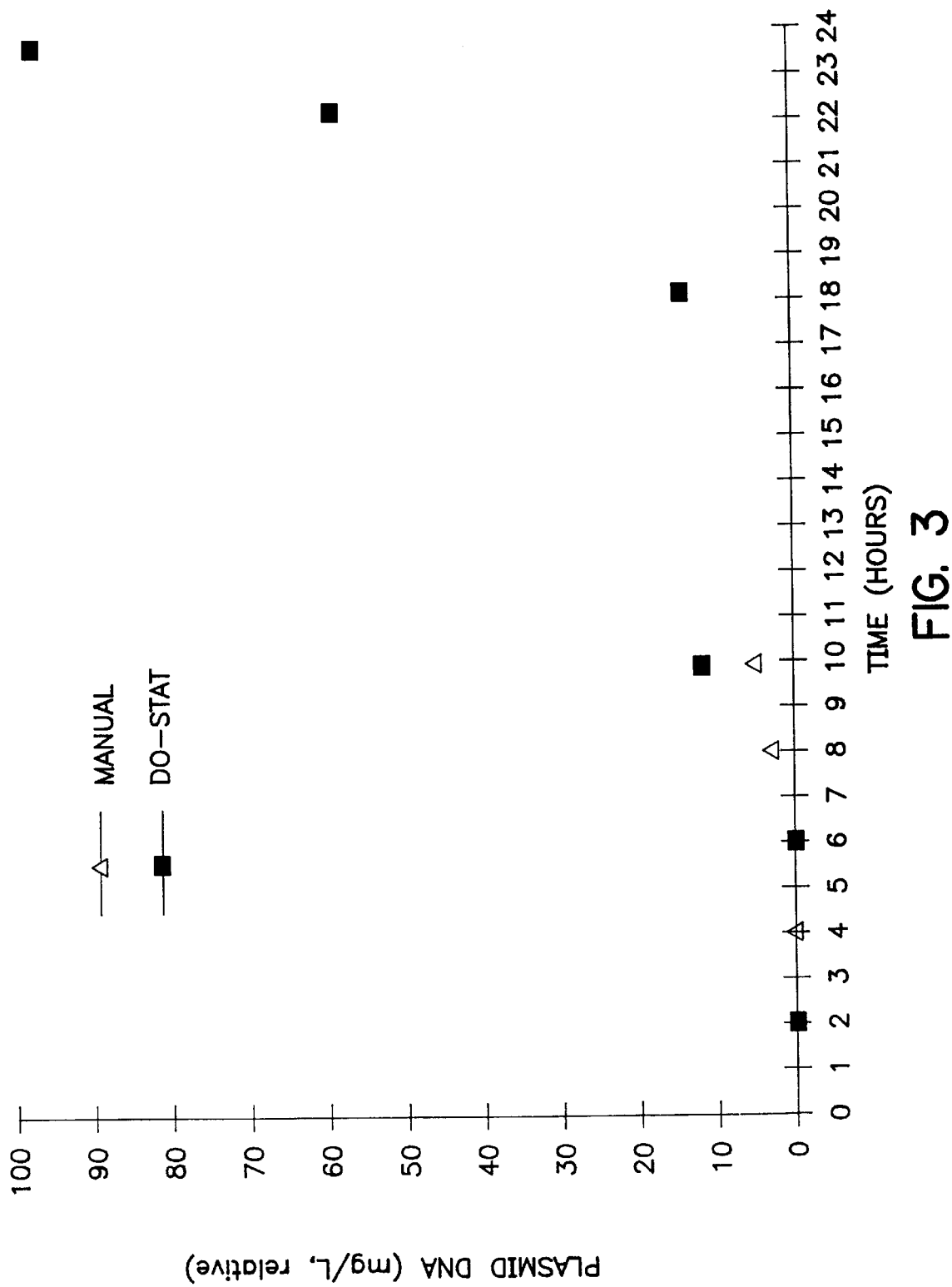
FIG. 3. Production of plasmid DNA in the DO/pH stat feed-back controlled fermentation and a manual fed-batch culture.

As shown in FIG. 3, final plasmid DNA yield increased about 10 fold in the DO/pH stat feed-back controlled process described in this invention, as compared to the manual controlled fed-batch culture. The improvement in plasmid DNA production is probably due to a combination of increased cell mass, an increased plasmid copy number resulting from the reduced cell growth rate and an optimized nutrient environment. This process has been successfully scaled up to SOL and 300L production fermentors with a similar performance as was obtained in the 7L scale.

I claim:

1. A method for producing high yields of plasmid DNA in a culture of *E. coli* containing said plasmid DNA, comprising reducing the cell growth rate of said *E. Coli* cells in culture by simultaneous feedback steps which maintain a desired pH and DOC, said method comprising the steps of:

(a) monitoring the pH of said culture and adding base to said culture when said pH drops below a first setpoint between pH 6.8 and 7.0;

(b) monitoring the pH of said culture and adding nutrient medium to said culture when said pH increases above a second setpoint between pH 7.05 to 7.2;

(c) monitoring the DOC of said culture and increasing agitation speed in said culture when said DOC decreases below a first DOC setpoint of between 10 to 50%, and maintaining said increased agitation speed once said first DOC setpoint is reached; and (d) monitoring the DOC of said culture and adding nutrient medium to said culture when said DOC increases above a second DOC setpoint of between 40 and 70%;

wherein plasmid DNA production by said culture is maximized and protein and RNA production by said culture is decreased.

2. The method according to claim 1, wherein said maintaining step comprises monitoring the pH of said culture with a pH controller, which automatically initiates the addition of base to said culture when said pH drops below a setpoint between pH 6.8 and 7.0.

3. The method according to claim 1, wherein said first setpoint is pH 7.0.

4. The method according to claim 1, wherein said second setpoint is between pH 7.1 and 7.2.

5. The method according to claim 4, wherein said second setpoint is pH 7.2.

6. The method according to claim 1, wherein said first DOC setpoint is between 20 and 40%.

7. The method according to claim 6, wherein said first DOC setpoint is 30%.

8. The method according to claim 1, wherein said agitation speed is increased 1% every 30 seconds for each instance that said DOC decreases below said first DOC setpoint.

9. The method according to claim 1, wherein said second DOC setpoint is between 45 and 55%.

10. The method according to claim 9 wherein said second DOC setpoint is 50%.

11. The method according to claim 1, further comprising ceasing nutrient medium addition when said DOC decreases below 50% and pH is less than 7.2 in said culture.

12. The method according to claim 1, wherein said cell growth rate is an average maximum specific cell growth rate of 0.4 $h^{-1}$.

13. The method according to claim 1, wherein the temperature of said *E. coli* cell culture ranges from about 30° C. to about 37° C.

14. The method according to claim 1, wherein said plasmid is a recombinant plasmid which contains a gene encoding a desired polypeptide suitable for expression in a mammalian cell.

15. A method for producing high yields of plasmid DNA in a culture of *E. coli* containing said plasmid DNA, comprising reducing the cell growth rate of said *E. coli* cells in culture by simultaneous automated feedback steps which maintain a desired pH and DOC, said method comprising the steps of:

(a) monitoring the pH of said culture and adding base to said culture when said pH drops below a first setpoint between pH 6.8 and 7.0;

(b) monitoring the pH of said culture and adding nutrient medium to said culture when said pH increases above a second setpoint between pH 7.05 to 7.2;

(c) monitoring the DOC of said culture and increasing agitation speed in said culture when said DOC decreases below a first DOC setpoint of between 10 to 50%, and maintaining said increased agitation speed once said first DOC setpoint is reached; and (d) monitoring the DOC of said culture and adding nutrient medium to said culture when said DOC increases above a second DOC setpoint of between 40 and 70%;

wherein plasmid DNA production by said culture is maximized and protein and RNA production by said culture is decreased.

16. The method according to claim 15, comprising monitoring said pH with a pH controller.

17. The method according to claim 16, wherein said pH controller controls one or more peristaltic pumps.

18. The method according to claim 17, wherein said pH controller controls one or more peristaltic pumps indirectly using computer software.

19. The method according to claim 15, comprising monitoring said DOC with a DOC controller.

20. The method according to claim 19, wherein said DOC controller controls one or more peristaltic pumps.

21. The method according to claim 20, wherein said DOC controller controls one or more peristaltic pumps indirectly using computer software.

22. The method according to claim 15, wherein said first setpoint is pH 7.0.

23. The method according to claim 15, wherein said second setpoint is between pH 7.1 and 7.2.

24. The method according to claim 23, wherein said second setpoint is pH 7.2.

25. The method according to claim 15, wherein said first DOC setpoint is between 20 and 40%.

26. The method according to claim 25, wherein said first DOC setpoint is 30%.

27. The method according to claim 15, wherein said agitation speed is increased 1% every 30 seconds for each instance that said DOC decreases below said first DOC setpoint.

28. The method according to claim 15, wherein said second DOC setpoint is between 45 and 55%.

29. The method according to claim 28, wherein said second DOC setpoint is 50%.

30. The method according to claim 15, further comprising ceasing nutrient medium addition when said DOC decreases below 50% and pH is less than 7.2 in said culture.

31. The method according to claim 15, wherein said cell growth rate is an average maximum specific cell growth rate of 0.4 $h^{-1}$.

32. The method according to claim 15, wherein the temperature of said *E. coli* cell culture ranges from about 30° C. to about 37° C.

33. The method according to claim 15, wherein said plasmid is a recombinant plasmid which contains a gene encoding a desired polypeptide suitable for expression in a mammalian cell.

* * * * *

UNITED STATES PATENT AND TRADEMARK OFFICE
CERTIFICATE OF CORRECTION

PATENT NO.    : 5,955,323
DATED         : September 21, 1999
INVENTOR(S)   : Wei Chen It is certified that error appears in the above-identified patent and that said Letters Patent is hereby corrected as shown below:

Col. 1, line 36, replace "optical" with -- optimal --.

Col. 3, line 65, replace "log" with -- 10g --.

Col. 4, line 56, replace "nave" with -- have --.

Col. 5, line 39, replace "agitatio" with -- agitation --.

Col. 5, line 45, replace "to-grow" with -- to grow --.

Col. 6, line 37, replace "SOL" with -- 80L --.

Signed and Sealed this

Eighteenth Day of July, 2000

Attest:

Q. TODD DICKINSON

*Attesting Officer*          *Director of Patents and Trademarks*